(12) United States Patent
Lim et al.

(10) Patent No.: US 8,798,049 B2
(45) Date of Patent: Aug. 5, 2014

(54) TRANSMITTER, RECEIVER AND METHOD THEREOF IN HUMAN BODY COMMUNICATION SYSTEM

(75) Inventors: In Gi Lim, Daejeon (KR); Hyung-Il Park, Daejeon (KR); Chang Hee Hyoung, Daejeon (KR); Sung Weon Kang, Daejeon (KR); Jung Hwan Hwang, Daejeon (KR); Tae Wook Kang, Daejeon (KR); Kyungsoo Kim, Daejeon (KR); Jung Bum Kim, Daejeon (KR); Sung Eun Kim, Seoul (KR); Jin Kyung Kim, Daejeon (KR); Kyung Hwan Park, Daejeon (KR); Byoung Gun Choi, Daegu (KR); Tae Young Kang, Seoul (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 141 days.

(21) Appl. No.: 13/369,214

(22) Filed: Feb. 8, 2012

(65) Prior Publication Data

US 2012/0201235 A1 Aug. 9, 2012

(30) Foreign Application Priority Data

Feb. 8, 2011 (KR) .................. 10-2011-0011207
Jan. 19, 2012 (KR) .................. 10-2012-0006394

(51) Int. Cl.
*H04L 12/28* (2006.01)
(52) U.S. Cl.
USPC .......................................... 370/389; 370/392
(58) Field of Classification Search
USPC .......... 370/349, 355, 357, 389, 392, 902, 912; 128/899; 600/109, 160, 112–114, 600/117–118, 120, 126, 145, 146; 340/286.07, 539.24, 620, 853.2
See application file for complete search history.

(56) References Cited

U.S. PATENT DOCUMENTS

| | | | | |
|---|---|---|---|---|
| 2006/0173265 | A1* | 8/2006 | Kim et al. .................. | 600/407 |
| 2006/0243288 | A1* | 11/2006 | Kim et al. .................. | 128/899 |
| 2008/0086654 | A1* | 4/2008 | Sogabe et al. .............. | 713/501 |
| 2008/0119691 | A1* | 5/2008 | Yagi et al. .................. | 600/109 |
| 2010/0130818 | A1* | 5/2010 | Jung et al. .................. | 600/109 |

FOREIGN PATENT DOCUMENTS

| KR | 1020040068424 A | 7/2004 |
|---|---|---|
| KR | 1020040068425 A | 7/2004 |

\* cited by examiner

*Primary Examiner* — Gary Mui
*Assistant Examiner* — Kabir Jahangir

(57) ABSTRACT

A receiver in a human communication system includes: receiving electrodes including a transmission frame including control frames and data frames; first and second switches connected with the receiving electrodes; a switching control unit controlling a switching of the first and second switches to selectively connect the receiving electrodes with the first and second switches in response to each control frame according to a predetermined rule every time each of the control frames is input; a signal processing unit performing signal processing on the transmission frame output from the first and second switches; a preamble detection unit detecting the first preamble from each of the control frames included in the signal-processed transmission frame to generate preamble correlation values for the first preamble; and a correlation value processing unit controlling the switching control unit to select pairs of final receiving electrodes among the receiving electrodes based on the preamble correlation values.

13 Claims, 5 Drawing Sheets

TRANSMITTER, RECEIVER AND METHOD THEREOF IN HUMAN BODY COMMUNICATION SYSTEM

CROSS-REFERENCES TO RELATED APPLICATIONS

The present application claims priority under 35 U.S.C. 119(a) to Korean Application No. 10-2011-0011207, filed on Feb. 8, 2011 and Korean Application No. 10-2012-0006394, filed on Jan. 19, 2012, in the Korean Intellectual Property Office, which is incorporated herein by reference in its entirety set forth in full.

BACKGROUND

Exemplary embodiments of the present invention relates to a transmitter, a receiver, and a method thereof in a human body communication system, and more particularly, to a transmitter, a receiver, and a method thereof in a human body communication system capable of more efficiently and stably transmitting and receiving data by selecting a combination of optimal receiving electrodes when two transmitting electrodes and a plurality of receiving electrodes are used in the human body communication system used for a capsule type endoscope, or the like.

A background art of the present invention is disclosed in Korean Patent No. 0522132 (Published in Oct. 10, 2005).

Various sensing apparatuses for collecting medical information from an inside of a human body have developed. However, it is very important to develop a technology of transmitting collected information to an outside of a human body in addition to the information collecting technology.

An example of a general data transmission method may include a communication cable scheme used for an endoscope, which has been developed for observing an internal state of a stomach. The communication cable scheme mainly inserts a cable configured of a wire or an optical fiber into a human body through a patient's throat. The communication cable scheme has high reliability and makes quality of data collected from the inside of the human body, but causes a severe pain to patients that will be subjected to an endoscopic operation.

In order to solve the problems, Given Imaging Co. in Israel developed a capsule type endoscope of brand name 'M2A'. The capsule type endoscope is a tablet form unlike the existing gastroscope or colonoscope. Therefore, when a user eats the capsule type endoscope through a mouth, images of the inside of a gullet, a stomach, a small intestine, and a large intestine are photographed by an image sensor in the capsule type endoscope. Further, the capsule type endoscope may transmit the photographed image data to a receiver at the outside of the human body through wireless communication and may be stored in the receiver.

However, the capsule type endoscope adopts a radio wave scheme as a signal transmission scheme and as a result, may consume a considerable amount of power, shorten operating time, be interfered with various electromagnetic waves from the outside of the human body, and have a degraded receiving sensitivity, Further, the capsule type endoscope includes a modulation circuit converting video signals into high frequency signals, and a wireless transmitter such as an antenna for transmitting signals, or the like, and as a result, may have an increased volume, increase production costs, and damage the human body due to the use of the high frequency. Therefore, a human body communication system capable of transmitting data in the inside of the human body to the outside of the human body by low frequency current using the human body as a wire.

However, in the human body communication system in accordance with the related art, current is generated by a potential difference between the transmitting electrodes formed on a surface of a capsule type endoscope injected into the human body and flows through the human body to induce voltage between two receiving electrodes mounted on the surface of the human body, thereby allowing the receiving apparatus to receive the data in the human body. However, in the case in which only the two receiving electrodes are used as described above, voltage is not induced or becomes small in the receiving electrode when a direction of current is vertical to an arrangement direction of the receiving electrodes, such that a receiving apparatus at the outside of the human body cannot accurately receive the signal transmitted from the capsule type endoscope.

Further, when the current generated by the potential difference between the transmitting electrodes of the capsule type endoscope reaches the receiving electrodes through the human body, the voltage is induced according to a distance between the transmitting electrode and the receiving electrode. In actual, when the signals transmitted from the inside of the human body reach the receiving electrodes through the human body, the voltage value is reduced from several thousand of times to tens of thousands of times and the signal interference occurs due to electromagnetic noises induced from the human body, such that the receiving electrodes cannot accurately receive the transmitting signals.

SUMMARY

An embodiment of the present invention is directed to a transmitter, a receiver, and a method thereof in a human body communication system capable of more efficiently and stably transmitting and receiving data by selecting a combination of optimal receiving electrodes when two transmitting electrodes and a plurality of receiving electrodes are used in the human body communication system used for a capsule type endoscope, or the like.

An embodiment of the present invention relates to a transmitter in a human body communication system, including: an image data generation unit generating image frames including image data regarding an obtained image; a transmission frame generation unit receiving the image frames to generate a transmission frame; and transmitting electrodes transmitting the transmission frame, wherein the transmission frame includes a plurality of control frames used for selecting pairs of receive electrodes in a receiver and a plurality of data frames including the image frames.

In one embodiment, the transmitter of claim 1, wherein each of the plurality of control frames includes: a first preamble used to synchronize the frames and select the receiving electrodes, a first header differentiating frame types, frame information including information on the image frames; and a switching time section for providing time required for electrode switching in the receiver, and each of the plurality of data frames includes: a second preamble synchronizing the frames, a second header differentiating the frame types; and at least a portion of the image frames.

In one embodiment, the number of plurality of control frames may be determined by the number of receiving electrodes in the receiver.

In one embodiment, the transmission frame generation unit may include: a data modulation unit modulating the image frames according to a preset modulation scheme; a preamble generation unit generating first and second preambles; a header generation unit generating first and second headers; a frame information generation unit generating frame information; and a multiplexer multiplexing the modulated image frame, the first and second preambles, the first and second headers, and a frame information and switching time section to generate the transmission frame.

Another embodiment of the present invention relates to a receiver in a human communication system, including: a plurality of receiving electrodes including a transmission frame including a plurality of control frames and a plurality of data frames; first and second switches connected with the plurality of receiving electrodes; a switching control unit controlling a switching of the first and second switches so as to selectively connect the plurality of receiving electrodes with the first and second switches in response to each control frame according to a predetermined rule every time each of the plurality of control frames is input; a signal processing unit performing signal processing by amplifying the transmission frame output from the first and second switches and by performing filtering for noise elimination; a preamble detection unit detecting the first preamble from each of the plurality of control frames included in the signal-processed transmission frame to generate preamble correlation values for the first preamble; and a correlation value processing unit controlling the switching control unit so as to select pairs of final receiving electrodes among the plurality of receiving electrodes based on the preamble correlation values.

In another embodiment, the preamble correlation value may represent correlation of data obtained by comparing each of the first preambles with a predetermined reference preamble for each bit.

In another embodiment, the correlation processing unit may select two receiving electrodes corresponding to the first preamble having a highest absolute value between the predetermined reference correlation value and the preamble correlation value as the pairs of final receiving electrodes.

In another embodiment, each of the plurality of control frames may include: a first preamble used to synchronize the frames and select the final receiving electrodes, a first header differentiating frame types, frame information including information on the image frames; and a switching time section for providing time required to control switching in the switching control unit, and each of the plurality of data frames includes: a second preamble synchronizing the frames, a second header differentiating the frame types; and at least a portion of the image frames.

In another embodiment, the number of plurality of control frames may be determined by the number of the plurality of receiving electrodes.

In another embodiment, the receiver may further include: a demultiplexer demultiplexing the signal-processed transmission frame; a header processing unit demodulating a header section in an output from the demultiplexer; a data demodulation unit demodulating the image frames in the output from the demultiplexer when the frame type is a data frame as a result of determining the header demodulated in the header processing unit; and an image data processing unit processing the demodulated image frame.

Another embodiment of the present invention relates to a method for transmitting data used for a human body communication system, including: generating image frames including image data regarding an obtained image; generating a transmission frame including the image frames; and transmitting the transmission frame through transmitting electrodes, wherein the transmission frame includes a plurality of control frames used for selecting pairs of receive electrodes in a receiver and a plurality of data frames including the image frames.

Another embodiment of the present invention relates to a method for receiving data used in a human body communication system, including: receiving a transmission frame including a plurality of control frames and a plurality of data frames through a plurality of receiving electrodes; controlling, by a switching control unit, a switching of the first and second switches so as to selectively connect the plurality of receiving electrodes with the first and second switches in response to each control frame according to a predetermined rule every time each of the plurality of control frames is input; performing, by a signal processing unit, signal processing on the transmission frame output from the first and second switches; detecting, by a preamble detection unit, the first preamble from each of the plurality of control frames included in the signal-processed transmission frame to generate preamble correlation values for the first preamble; and controlling, by a correlation value processing unit, the switching control unit so as to select pairs of final receiving electrodes among the plurality of receiving electrodes based on the preamble correlation values.

BRIEF DESCRIPTION OF THE DRAWINGS

The above and other aspects, features and other advantages will be more clearly understood from the following detailed description taken in conjunction with the accompanying drawings, in which.

DESCRIPTION OF SPECIFIC EMBODIMENTS

Hereinafter, embodiments of the present invention will be described with reference to accompanying drawings. However, the embodiments are for illustrative purposes only and are not intended to limit the scope of the invention.

Figure 1:
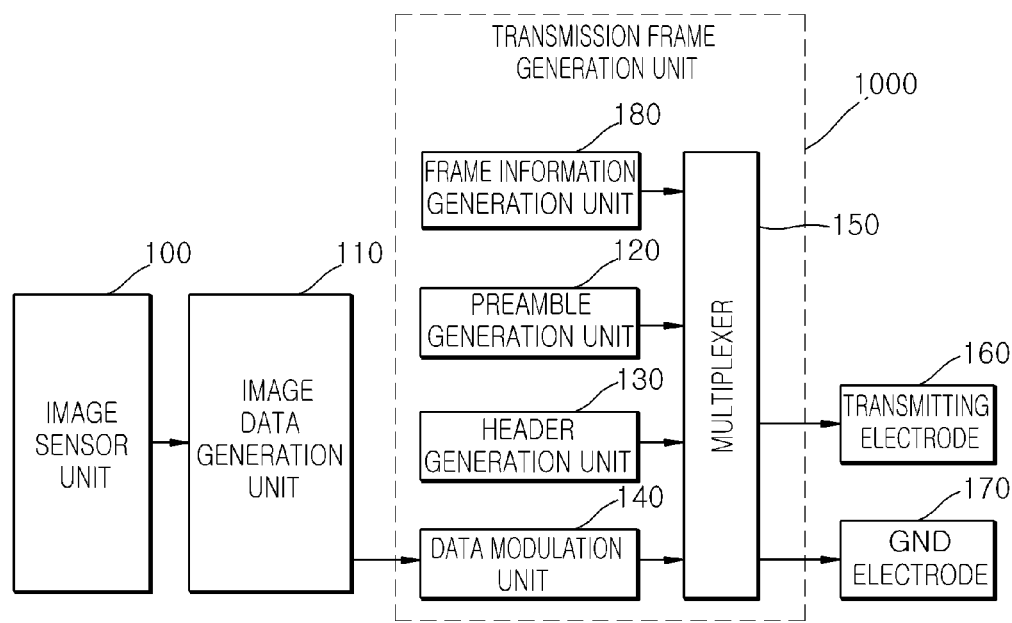
FIG. 1 is a diagram illustrating a configuration of a transmitter in accordance with an embodiment of the present invention.
Figure 2:
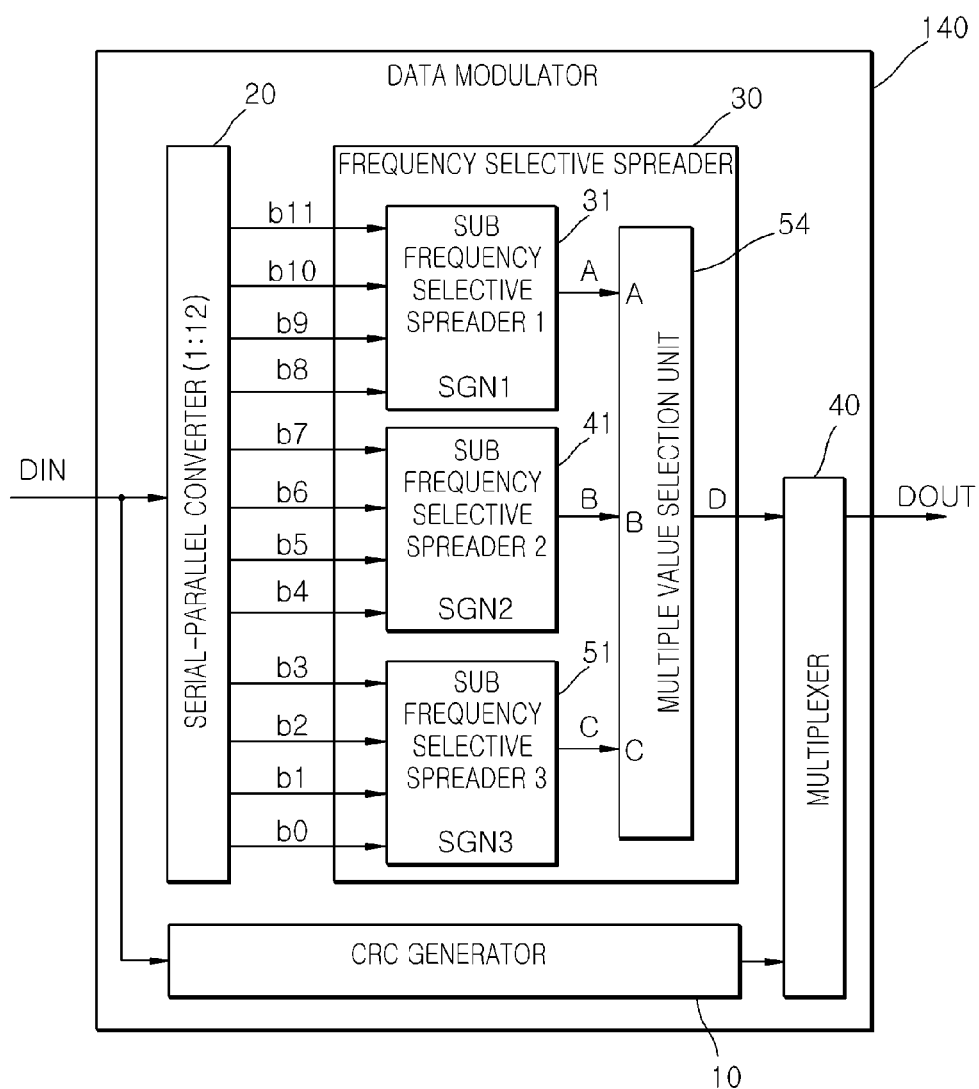
FIG. 2 is a diagram illustrating a configuration of a data modulation unit used for the transmitter in accordance with the embodiment of the present invention.
Figure 3:
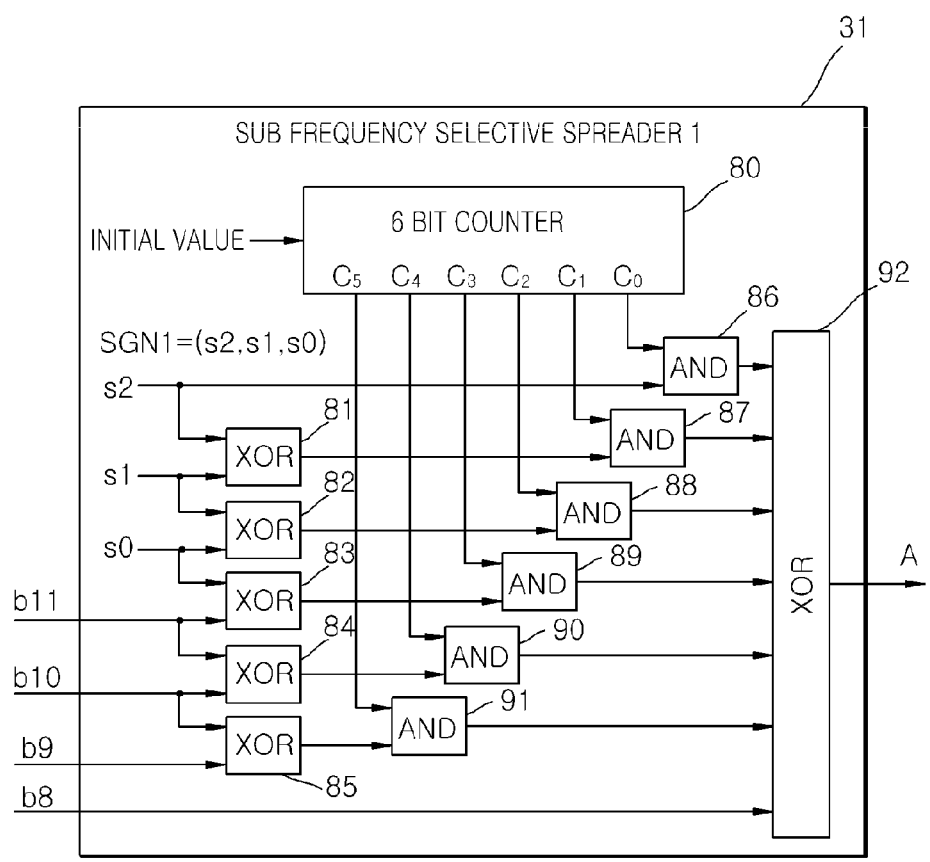
FIG. 3 is a diagram illustrating a configuration of a sub frequency selective spreader used for the data modulation unit of FIG. 2.
Figure 4:
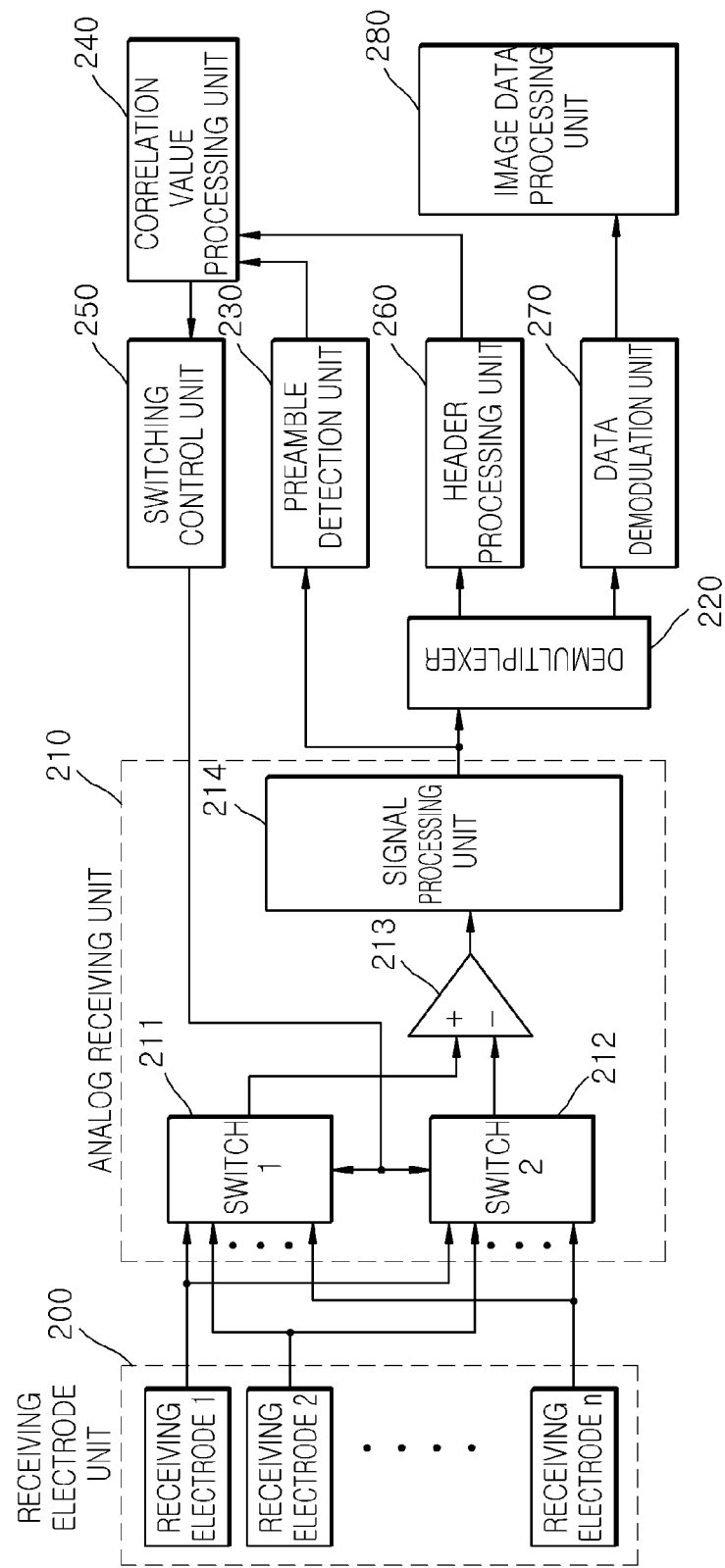
FIG. 4 is a diagram illustrating a configuration of a receiver in accordance with an embodiment of the present invention.
Figure 5:
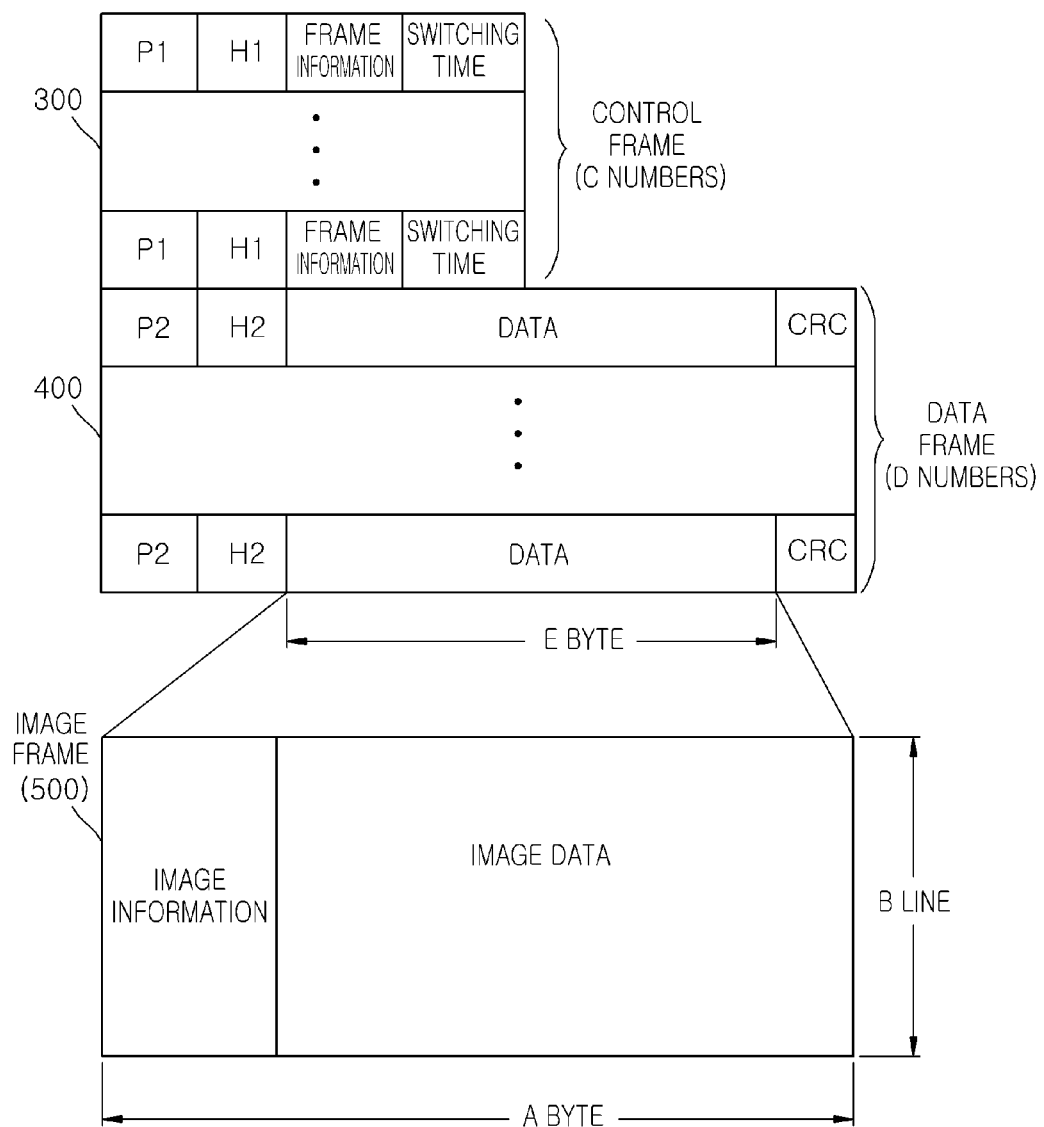
FIG. 5 is a diagram illustrating a configuration of a transmission frame used in the embodiment of the present invention.

FIG. 1 is a diagram illustrating a configuration of a transmitter in accordance with an embodiment of the present invention, FIG. 2 is a diagram illustrating a configuration of a data modulation unit used for the transmitter in accordance with the embodiment of the present invention, FIG. 3 is a diagram illustrating a configuration of a sub frequency selective spreader used for the data modulation unit of FIG. 2, FIG. 4 is a diagram illustrating a configuration of a receiver in accordance with an embodiment of the present invention, and FIG. 5 is a diagram illustrating a configuration of a transmission frame used in the embodiment of the present invention. Exemplary embodiments of the present invention will be described with reference to the accompanying drawings.

First, as illustrated in FIG. 5, a transmission frame used in a transmitter and a receiver in accordance with an embodiment of the present invention may include a plurality of control frames 300 used for selecting pairs of receiving electrodes in the receiver and a plurality of data frames 400 including an image frame 500.

Each of the plurality of control frames 300 may include a first preamble P1 used for synchronizing the frames and selecting the receiving electrodes, a first header H1 for differentiating a frame type, a frame information having information on the image frame 500, and a switching time section for providing time required for electrode switching in the receiver. Further, each of the plurality of data frames 400 may include a second preamble P2 for synchronizing the frames, a second header H2 for differentiating the frame types, and at least a portion of the image frame 500, and the detailed description thereof will be described below.

As illustrated in FIG. 1, a transmitter in a human body communication system in accordance with the embodiment of the present invention may include an image data generation unit 110 generating the image frame 500 including image data regarding image captured in the image sensor unit 100, a transmission frame generation unit 1000 receiving the image frame 500 to generate the transmission frame, and a transmitting electrode 160 for transmitting the transmission frame. Further, the transmission frame generation unit 1000 may include a data modulation unit 140 modulating the image frame 500 according to a preset modulation scheme, a preamble generation unit 120 generating first and second preambles P1 and P2, a header generation unit 130 generating first and second headers H1 and H2, a frame information generation unit 180 generating frame information, and a multiplexer 150 multiplexing the modulated image frame 500, the first and second preambles P1 and P2, the first and second headers H1 and H2, a frame information and switching time section to generate the transmission frame.

In addition, as illustrated in FIG. 4, a receiver in a human body communication system in accordance with the embodiment of the present invention may include a receiving electrode unit 200 including a plurality of receiving electrodes 1 to n including a transmission frame including a plurality of control frames 300 and a plurality of data frames 400, first and second switches 211 and 212 connected with the plurality of receiving electrodes 1 to n, a switching control unit 250 controlling a switching of the first and second switches 211 and 212 so as to selectively connect the plurality of receiving electrodes 1 to n with the first and second switches 211 and 212 in response to each control frame 300 according to a predetermined rule every time each of the plurality of control frames 300 is input, a signal processing unit 214 performing signal processing by amplifying the transmission frame output from the first and second switches 211 and 212 and by performing filtering for noise elimination, a preamble detection unit 230 detecting the first preamble P1 from each of the plurality of control frames 300 included in the signal-processed transmission frame to generate preamble correlation values for the first preamble P1, and a correlation value processing unit 240 controlling the switching control unit 250 so as to select pairs of final receiving electrodes among the plurality of receiving electrodes 1 to n based on the preamble correlation values.

In addition, the receiver in the human body communication system in accordance with the embodiment of the present invention may further include a demultiplexer 220 demultiplexing the signal-processed transmission frame, a header processing unit 260 demodulating a header section in an output from the demultiplexer 220, a data demodulation unit 270 demodulating the image frame 500 in the output from the demultiplexer 220 when the frame type is a data frame as a result of determining the header demodulated in the header processing unit 260, and an image data processing unit 280 processing the demodulated image frame 500.

Operation and action of the embodiment of the present invention configured as described above will be described in detail with reference to FIGS. 1 to 5.

The transmitter, the receiver, and the method thereof in the human body communication system in accordance with the embodiment of the present invention may be used for a transmission and reception method for a capsule type endoscope, for instance. The transmission frame structure used in the embodiment of the present invention includes a plurality (C numbers) of control frames 300 repeated at a short length for selecting the pairs of receiving electrodes among the plurality of receiving electrodes 1 to n of the receiver and a plurality (D numbers) of data frames 400 for transmitting the image data by using the selected pairs of receiving electrodes. Each of the control frames 300 is configured to include the first preamble P1, the first header H1, and the frame information and switching time and each of the data frames 400 is configured to include the second preamble P2, the second header H2, data, and cyclic redundancy check (CRC).

FIG. 1 illustrates a configuration of the transmitter in the human body communication system in accordance with the embodiment of the present invention. In FIG. 1, the image data generation unit 110 receives the images sensed by the image sensing unit 100 to generate the image data and adds the image information such as an image line number, or the like, to the image data to generate the image frame 500 of A byte B line as illustrated in FIG. 5.

As described above, the transmission frame generation unit 1000 may include the data modulation unit 140, the preamble generation unit 120, the header generation unit 130, the frame information generation unit 180, and the multiplexer 150.

The preamble generation unit 120 generates a predetermined length of preambles P1 and P2 for synchronizing frames at a start of the plurality of control frames 300 and a start section of the data frame 400. Herein, in order to differentiate the preamble P1 used for the control frames 300 and the preamble P2 used for the data frame 400, they are each represented by the first preamble P1 and the second preamble P2. The first preamble P1 used for each of the control frames 300 is used to select the pairs of receiving electrodes in the receiver.

The header generation unit 130 generates the headers H1 and H2 having a differentiator for differentiating the control frames 300 and the data frame 400 and frame control bits. In order to differentiate the header H1 used for the control frames 300 and the header H2 used for the data frame 400, they are each represented by the first header H1 and the second header H2.

Further, the frame information generation unit 180 generates the frame information. The frame information may include the information regarding the image frame such as an image frame number, an image exposure time, or the like.

The data modulation unit 140 modulates the image frame generated from the image data generation unit 110 according to a predetermined modulation scheme and provides the modulated image frame to the multiplexer 150. Herein, as the used modulation scheme, various types of modulation schemes may be used according to communication schemes, image data formats, or the like.

The multiplexer 150 adds the switching time to the generated first preamble P1, first header H1, and frame information to generate the plurality (C number) of control frames 300 and adds the CRC to the data that are the second preamble P2, the second header H2, and the image frame to generate the plurality (D numbers) of data frames 400. Here, the switching time is added to secure the time used to switch the plurality of receiving electrodes connected with two switches of the receiver. The CRC represents the cyclic redundancy check added to each end of the plurality of data frames 400.

The transmission frame including the generated control frames 300 and data frame 400 is transmitted through the transmitting electrode 160 and the control frames 300 and the data frame 400 will be described below in more detail.

Meanwhile, as an example of the modulation scheme used in the data modulation unit 140, the data modulation unit 140 may generate the data spread by a frequency selective digital transmission (FSDT) scheme using a frequency selective spreading code in accordance with the embodiment of FIG. 2.

FIG. 2 is a configuration example of the data modulation unit 140 in the transmitter in accordance with the embodiment of the present invention. The data modulation unit 140 is configured to include a CRC generator 10, a serial-parallel converter 20, a frequency selective spreader 30, and a multiplexer 40.

The image frame data input from the image data generation unit 110 are input to the serial-parallel converter 20 while being input to the CRC generator 10 in the data modulation unit 140. Further, 12 bit parallel symbols generated by the serial-parallel conversion process in the serial-parallel converter 20 are input to the frequency selective spreader 30. The input 12 bit parallel symbols are divided into 4 bits from the upper and input to the sub frequency selective spreaders 31, 41, and 51, respectively. If it is assumed that SGN1, SGN2, and SGN3 values within the sub frequency selective spreader 31, 41, and 51 for selecting a frequency are set to be "101", "110", and "111", the sub frequency selective spreader 1 31 selects as 3 bits of b11, b10, and b9 one of 8 Walsh codes W40 to W47 of subgroup 5 by input bits b11, b10, b9, and b8 and "101" that is the SGN1 value and outputs 64 bits as A in a form of 1 bitstream by XORing the selected value by b8. The sub frequency selective spreader 2 41 selects as 3 bits of b7, b6, and b5 one of 8 Walsh codes W48 to W55 of subgroup 6 by input bits b7, b6, b5, and b4 and "110" that is the SGN2 value and outputs 64 bits as B in a form of 1 bitstream by XORing the selected value by b4. The sub frequency selective spreader 3 51 selects as 3 bits of b3, b2, and b1 one of 8 Walsh codes W56 to W63 of subgroup 7 by input bits b3, b2, b1, and b0 and "111" that is the SGN3 value and outputs 64 bits as C in a form of 1 bitstream by XORing the selected value by b0.

Next, a multiple value selection unit 54 receives 3 bitstreams of A, B, and C output from each of the sub frequency selective spreaders 31, 41, and 51 and outputs D value according to the following Equation 1 as multiple values.

$$D=(A \text{ and } B) \text{ or } (B \text{ and } C) \text{ or } (C \text{ and } A)$$ [Equation 1]

In the above Equation 1, 'or' represents an OR gate and 'and' represents an AND gate.

The multiplexer 40 selects and outputs the output from the frequency selective spreader 30 and the CRC value generated from the CRC generator 10 according to the configuration of the data frame 400.

FIG. 3 illustrates a configuration of the sub frequency selective spreader 1 31 in accordance with the embodiment of the present invention. The sub frequency selective spreader 1 31 has a 6 bit counter 80 and has the frequency selective control bits s2, s1, and s0 of the 3 bits and the data input bits b11, b10, b9, and b8 of 4 bits. The 6 bit counter is reset to an initial value '0' for each symbol so as to count 0 to 63. The frequency selective control bits s2, s1, and s0 of 3 bits and the data input bits b11, b10, and b9 of 3 bits select and generate one of the 8 Walsh codes and A in the form of 1 bitstream is output by XOR-operating b8 among the input bits by the generated Walsh codes. In addition, for Gray indexing, five XOR logic circuits 81, 82, 83, 84, and 85 are provided. Further, 6 AND logic circuits 86, 87, 88, 89, 90, and 91 using C5 to C0 that are an output from the 6 bit counter, an uppermost bit s2 of the frequency selective control bit, and an output bit of the 5 XOR logic circuits, respectively, and an XOR logic circuit 92 is provided for XORing the output from the 6 AND logic circuits and b8 by the b8. The sub frequency selective spreader 2 41 and the sub frequency selective spreader 3 51 may be configured by the same method.

FIG. 4 illustrates a configuration example of the receiver in the human body communication system in accordance with the embodiment of the present invention, that is, a receiving apparatus for a capsule type endoscope In FIG. 4, the receiving electrode unit 200 including n receiving electrodes 1 to n is attached to each portion of the human body to receive signals transmitted from the transmitting apparatus in the human body and the output from the receiving electrodes 1 to n is connected with the first switch 211 and the second switch 212, respectively, of the analog receiving unit 210.

The first switch 211 and the second switch 212 receives the control signal of the switching control unit 250 and is selectively connected with the pairs of receiving electrodes, respectively, among n receiving electrodes 1 to n. The output from the first switch 211 is connected with a + terminal of a differential amplifier 213, the output from the second switch 212 is connected with a − terminal of the differential amplifier 213, and the differential amplifier 213 amplifies and outputs a difference of the voltage value between the two electrodes.

Then, the signal processing unit 214 receives the voltage difference of the pairs of receiving electrodes that are the output from the differential amplifier 213 and performs filtering for removing noise, signal amplification, clock and data recovery (CDR) for frequency and timing synchronization, or the like, on the input signal. The output from the signal processing unit 214 is provided to the preamble detection unit 230 and the demultiplexer 220.

The preamble detection unit 230 receives the output from the signal processing unit 214 to detect a predetermined length of first and second preambles P1 and P2 included in the plurality of control frames 300 and the data frame 400, thereby performing the frame synchronization and generating the preamble correlation value on the first preamble P1 included in each of the plurality of control frames 300. Here, the preamble correlation value represents the data correlation obtained by comparing each of the detected first preambles with the predetermined reference preambles for each bit.

Describing the preamble of 10 bit length as an example, if any first preamble is '1111100111' when the predetermined reference preamble is '1111100000', the number of bits having the same value is 7 and the number of different bits is 3, such that the preamble correlation value that is the data correlation may be 7. In addition, when the number of bits having the same value is 2 and the number of different bits is 8, the preamble correlation value may be 2. That is, when calculating the preamble correlation values for each of the first preambles P1 of the plurality of control frames 300, it can be appreciated that as the value is large, the accuracy of data against the reference preamble is high as much. In addition, since the first switch 211 is connected to (+) terminal of the differential amplifier 213 and the second switch 212 is connected to (−) terminal of the differential amplifier 213, the inverting signal having an inverted sign may be output from the differential amplifier 213 and the signal processing unit 214 according to the order or the position in which each pair of receiving electrodes is connected with the first switch 211 and the second switch 212. In this case, it can be appreciated that as the value is low, the accuracy of data to reference preamble is increased even though the preamble correlation value is relatively low. Therefore, it can be appreciated that an absolute value of the difference between the predetermined reference correlation value having an intermediate level and each preamble correlation value is calculated and the data received through a combination of pairs of receiving electrodes receiving the corresponding control frames 300 including the first preamble P1 having a relatively large absolute value have the high accuracy as much, which may be a reference determining the pairs of final receiving electrodes in the receiving electrodes 1 to n at the following stage.

In accordance with the embodiment of the present invention, at the time of calculating the preamble correlation value, the operation different from the above description is performed on the number of same bits and the number of different bits to obtain the correlation value. If the correlation value is a correlation value capable of representing the data accuracy between the reference preamble and the corresponding preamble, the correlation value may be determined according to the design's intention even by any calculation method.

Meanwhile, the demultiplexer 220 performs the demultiplexing on the signal-processed transmission frame and the header processing unit 260 extracts the first header H1 and the second header H2 in the output signal obtained through the demultiplexing to demodulate the frame differentiator and the frame control bits. In this case, when the received frame differentiator is the control frame, the frame correlation value and the frame control bit generated in the preamble detection unit 230 are provided to the correlation value processing unit 240.

The correlation value processing unit 240 starts from the combination of pairs of basic receiving electrodes every time the preamble correlation value and the frame control bit are input to receive and store the preamble correlation value obtained by continuously updating the combination of pairs of receiving electrodes based on an order defined according to the number of receiving electrodes from the preamble detection unit 230 and finally selects the pairs of receiving electrodes corresponding to the preamble in which the absolute value between the above reference correlation value and the preamble correlation value is a maximum value.

To this end, there is a need to require the switching control of the switching control unit 250, wherein the switching control unit 250 starts from the combination of pairs of basic receiving electrodes every time each of the plurality of control frames 300 is received through the receiving electrodes 1 to n to continuously update the combination of pairs of receiving electrodes based on an order defined according to the number of receiving electrodes 1 to n, thereby performing the switching control on the first switch 211 and the second switch 212. To this end, the switching control unit 250 may receive the information on the combination or current receiving electrodes from the correlation value processing unit 240 and generates the control signals for switching the first switch 211 and the second switch 212 within an analog receiving unit 210 for "switching time" included in each control frame. Here, the combination of pairs of basic receiving electrodes and the defined order are determined as the order of the receiving electrodes representing the optimal receiving state based on a plurality of clinical experiments. That is, since the combination of pairs of corresponding receiving electrodes for each control frame is selected, the pairs of C receiving electrodes for C control frames are selected and may be connected with the first and second switches 211 and 212.

When the pairs of receiving electrodes having the highest receiving sensitivity or the excellent accuracy are determined by the above process and the frame differentiator demodulated in the header processing unit 260 is the data frame, a data demodulator 270 receives the output from the demultiplexer 220 to perform the demodulation and then, transmits the demodulated data to an image data processing unit 280. Further, the image data processing unit 280 performs and outputs the signal processing on the demodulated image frame.

Through the above process, the transmitted image data within the human body communication system may be provided to the user in an image form having the optimal accuracy through the pairs of optimal receiving electrodes.

Meanwhile, FIG. 5 illustrates a configuration diagram of the transmission frame in accordance with the embodiment of the present invention.

The image data generation unit 110 generates the image frame 500 of A byte B line by adding the image data and the image information read from the image sensing unit 100. In order to transmit one generated image frame 500, the transmission frame is configured to include the C control frames 300 having a short length and the D data frames 400.

The control frame 300 is configured to include the first preamble P1, the first header H1, the frame information, and the switching time for selecting the pairs of optimal receiving electrodes, wherein the first preamble P1 is used for the control frame synchronization and the calculation of the preamble correlation value. Further, the first header H1 includes the frame differentiator, other frame control bits, or the like, and informs whether the received frame is the control frame or the data frame. The frame information may include the information regarding the image frame such as the image frame number, the image exposure time, or the like and the predetermined time of switching time is used to selectively switch the pairs of two receiving electrodes among the plurality of receiving electrodes 1 to n in the first switch 211 and the second switch 212 in the receiver as described above.

The number C of control frames 300 is determined by the number n of a plurality of receiving electrodes 1 to n and may be set to be the same value as $_nC_2$ meaning the number of cases selecting two different receiving electrodes among n. Thereby, the receiver may receive each of the C control frames 300 through each of the combination of pairs of possible receiving electrodes selectable among the plurality of receiving electrodes 1 to n and may determine as the pairs of optimal receiving electrodes the combination of pairs of final receiving electrodes having the highest signal receiving accuracy and the excellent receiving sensitivity by comparing the frame correlation values for each of the received C control frames 300. As described above, the work of selecting the combination of pairs of final receiving electrodes is performed in the correlation value processing unit 240 and the switching control unit 250 controlled thereby performs the switching control on the first switch 211 and the second switch 212 so as to receive the data frame 400 through the pairs of final receiving electrodes.

Further, the data frame 400, which is a frame for transmitting the image frame 500 by using the pair of final receiving electrodes determined by the control frames 300, is configured to include the second preamble P2, the second header H2, the data, and the CRC. The second preamble P2 may use the preamble like the control frames 300 and the second header H2 may include the data frame information like the frame differentiator and the data line number representing the data frame. The data of E byte are input from the image data 500 and the input data generates the CRC value to be added and transmitted after the data of E byte are transmitted. The number D of data frames 400 and the data length E byte have the relationship Equation like the following Equation 2 with respect to A byte B line of the image frame.

$$A\text{ Byte} \times B\text{ Line} = E\text{ Byte} \times D\text{ Number (Number of Data Frame)} \qquad \text{[Equation 2]}$$

As described above, in accordance with the embodiment of the present invention, when the two transmitting electrodes and the plurality of receiving electrodes are used in the human body communication system used for the capsule type endoscope, or the like, it is possible to more efficiently and stably transmit and receive data by selecting the combination of optimal receiving electrodes.

The embodiments of the present invention can provide the transmitter, the receiver, and the method thereof in the human body communication system capable of more efficiently and stably transmitting and receiving data by selecting the combination of optimal receiving electrodes when the two transmitting electrodes and the plurality of receiving electrodes are used in the human body communication system used for the capsule type endoscope, or the like.

The embodiments of the present invention have been disclosed above for illustrative purposes. Those skilled in the art will appreciate that various modifications, additions and substitutions are possible, without departing from the scope and spirit of the invention as disclosed in the accompanying claims.

What is claimed is:

1. A transmitter, comprising:
   an image data generation unit generating image frames including image data regarding an obtained image;
   a transmission frame generation unit receiving the image frames to generate a transmission frame; and
   transmitting electrodes transmitting the transmission frame,
   wherein the transmission frame includes a plurality of control frames used for selecting pairs of receiving electrodes in a receiver and a plurality of data frames including the image frames,
   wherein each of the plurality of control frames includes:
      a first preamble used to synchronize the frames and select the receiving electrodes;
      a first header differentiating frame types;
      frame information including information on the image frames; and
      a switching time section for providing time required for electrode switching in the receiver, and
   each of the plurality of data frames includes:
      a second preamble synchronizing the frames;
      a second header differentiating the frame types; and
      at least a portion of the image frames; and
   the transmission frame generation unit includes:
      a data modulation unit modulating the image frames according to a preset modulation scheme;
      a preamble generation unit generating the first and second preambles;
      a header generation unit generating the first and second headers;
      a frame information generation unit generating the frame information; and
      a multiplexer multiplexing the modulated image frame, the first and second preambles, the first and second headers, and the frame information and the switching time section to generate the transmission frame.

2. The transmitter of claim 1, wherein a number of the plurality of control frames is determined by a number of the receiving electrodes in the receiver.

3. A receiver in a human communication system, comprising:
   a plurality of receiving electrodes receiving a transmission frame including a plurality of control frames and a plurality of data frames;
   first and second switches connected with the plurality of receiving electrodes;
   a switching control unit controlling a switching of the first and second switches so as to selectively connect the plurality of receiving electrodes with the first and second switches in response to each control frame according to a predetermined rule when each of the plurality of control frames is input;
   a signal processing unit performing a signal processing on the transmission frame output from the first and second switches;
   a preamble detection unit detecting a first preamble from each of the plurality of control frames included in the signal-processed transmission frame to generate a preamble correlation value for the first preamble; and
   a correlation value processing unit controlling the switching control unit so as to select a pair of final receiving electrodes among the plurality of receiving electrodes based on the preamble correlation value,
   wherein the preamble correlation value represents a degree of correlation between a value of the first preamble and a value of a predetermined reference preamble and is obtained by performing a bitwise comparison on each bit of the value of the first preamble and a corresponding bit of the value of the predetermined reference preamble.

4. The receiver of claim 3, wherein the correlation processing unit selects the pair of final receiving electrodes corresponding to the first preamble having a highest absolute difference between the preamble correlation value corresponding to the pair of final receiving electrodes and a predetermined reference correlation value, the predetermined reference correlation value having an intermediate level.

5. The receiver of claim 3, wherein:
   each of the plurality of control frames includes:
      the first preamble used to synchronize the frames and select the pair of final receiving electrodes;
      a first header differentiating frame types;
      frame information including information on the image frames; and
      a switching time section for providing a time required for switching control in the switching control unit, and
   each of the plurality of data frames includes:
      a second preamble synchronizing the frames;
      a second header differentiating the frame types; and
      at least a portion of the image frames.

6. The receiver of claim 5, wherein a number of the plurality of control frames is determined by a number of the plurality of receiving electrodes.

7. The receiver of claim 5, further comprising:
   a demultiplexer demultiplexing the signal-processed transmission frame;
   a header processing unit demodulating a header section in an output from the demultiplexer;
   a data demodulation unit demodulating the image frames in the output from the demultiplexer when the frame type is a data frame as a result of determining the header section demodulated in the header processing unit; and
   an image data processing unit processing the demodulated image frame.

8. A method for transmitting data used for a human body communication system, comprising:

generating image frames including image data regarding an obtained image;
generating a transmission frame including the image frames; and
transmitting the transmission frame through transmitting electrodes;
wherein the transmission frame includes a plurality of control frames used for selecting pairs of receiving electrodes in a receiver and a plurality of data frames including the image frames;
wherein each of the plurality of control frames includes:
a first preamble used to synchronize the frames and select the receiving electrodes;
a first header differentiating frame types;
frame information including information on the image frames; and
a switching time section for providing time required for electrode switching in the receiver, and
each of the plurality of data frames includes:
a second preamble synchronizing the frames;
a second header differentiating the frame types; and
at least a portion of the image frames, and
wherein the generating of the transmission frame includes:
modulating the image frame according to a preset modulation scheme;
generating the first and second preambles;
generating the first and second headers;
generating the frame information; and
multiplexing the modulated image frame, the first and second preambles, the first and second headers, and the frame information and the switching time section to generate the transmission frame.

9. The method of claim 8, wherein a number of the plurality of control frames is determined by a number of the receiving electrodes in the receiver.

10. A method for receiving data used in a human body communication system, comprising:
receiving a transmission frame including a plurality of control frames and a plurality of data frames through a plurality of receiving electrodes;
controlling, by a switching control unit, a switching of first and second switches so as to selectively connect the plurality of receiving electrodes with the first and second switches in response to each control frame according to a predetermined rule when each of the plurality of control frames is input;
performing, by a signal processing unit, a signal processing on the transmission frame output from the first and second switches;
detecting, by a preamble detection unit, a first preamble from each of the plurality of control frames included in the signal-processed transmission frame to generate a preamble correlation value for the first preamble; and
controlling, by a correlation value processing unit, the switching control unit to select a pair of final receiving electrodes among the plurality of receiving electrodes based on the preamble correlation value,
wherein the preamble correlation value represents a degree of correlation between a value of the first preamble and a value of a predetermined reference preamble and is obtained by performing a bitwise comparison on each bit of the value of the first preamble and a corresponding bit of the value of the predetermined reference preamble.

11. The method of claim 10, wherein two receiving electrodes corresponding to the first preamble having a highest absolute difference between the preamble correlation value and a predetermined reference correlation value having an intermediate level are selected as the pair of final receiving electrodes.

12. The method of claim 10, wherein each of the plurality of control frames includes:
a first preamble used to synchronize the frames and select the final receiving electrodes,
a first header differentiating frame types,
frame information including information on the image frames; and
a switching time section for providing time required for switching control in the switching control unit, and
each of the plurality of data frames includes:
a second preamble synchronizing the frames;
a second header differentiating the frame types; and
at least a portion of the image frames.

13. The method of claim 12, wherein a number of the plurality of control frames is determined by a number of the plurality of receiving electrodes.

\* \* \* \* \*